US012788341B2

(12) United States Patent
Jacob et al.

(10) Patent No.: US 12,788,341 B2
(45) Date of Patent: Nov. 10, 2026

(54) RADIATION SENSOR WITH INTEGRATED ELECTRONICS

(71) Applicant: GE Precision Healthcare LLC, Waukesha, WI (US)

(72) Inventors: Biju Jacob, Niskayuna, NY (US); William Hennessy, Troy, NY (US); Brian Yanoff, Niskayuna, NY (US); Nicholas Konkle, Sussex, WI (US)

(73) Assignee: GE Precision Healthcare LLC, Waukesha, WI (US)

(*) Notice: Subject to any disclaimer, the term of this patent is extended or adjusted under 35 U.S.C. 154(b) by 66 days.

(21) Appl. No.: 19/059,025

(22) Filed: Feb. 20, 2025

(65) Prior Publication Data

US 2026/0240510 A1 Aug. 20, 2026

(51) Int. Cl.
*A61B 6/42* (2024.01)
*A61B 6/03* (2006.01)

(52) U.S. Cl.
CPC .............. *A61B 6/4241* (2013.01); *A61B 6/03* (2013.01); *A61B 6/4233* (2013.01)

(58) Field of Classification Search
CPC ........ A61B 6/03; A61B 6/4233; A61B 6/4241
See application file for complete search history.

(56) References Cited

U.S. PATENT DOCUMENTS

| | | | | | |
|---|---|---|---|---|---|
| 5,187,380 | A * | 2/1993 | Michon | H10F 30/29 | 257/E31.09 |
| 5,886,353 | A * | 3/1999 | Spivey | A61B 6/4233 | 250/580 |
| 8,785,876 | B2 | 7/2014 | Tajima | | |
| 2001/0034105 | A1* | 10/2001 | Carlson | H10D 62/106 | 438/380 |
| 2003/0059630 | A1* | 3/2003 | Carlson | H10F 30/221 | 257/E27.129 |
| 2003/0218120 | A1* | 11/2003 | Shibayama | H10F 39/199 | 250/214.1 |
| 2004/0120453 | A1* | 6/2004 | Vafi | G01T 1/20182 | 378/19 |
| 2006/0065846 | A1* | 3/2006 | Ertel | G01T 1/2006 | 250/370.11 |
| 2007/0064139 | A1* | 3/2007 | Nagase | H10F 39/011 | 348/311 |

(Continued)

*Primary Examiner* — Blake C Riddick
(74) *Attorney, Agent, or Firm* — Foley & Lardner LLP

(57) ABSTRACT

A computed tomography (CT) imaging system includes a detector array configured to detect X-ray projections. The detector array includes a semiconductor sensor array having a plurality of sensors. Each sensor includes a first surface, a second surface, a substrate, and a readout electronics unit. The first surface has a high-voltage bias and includes a first dopant and can receive the X-ray projections. The second surface is opposite the first surface and includes a plurality of sensing regions of a second dopant. The second surface has a low-voltage bias and is configured to collect charges from the X-ray projections. The substrate includes a semiconductor material with a resistivity of at least five kiloohm centimeters and is positioned between the first and second surfaces. The readout electronics unit is positioned between the sensing regions. A surface area of the readout electronics unit is less than one percent of the second surface.

20 Claims, 11 Drawing Sheets

(56) References Cited

U.S. PATENT DOCUMENTS

| | | | | |
|---|---|---|---|---|
| 2008/0112535 | A1* | 5/2008 | Wojcik | A61B 6/4233 250/366 |
| 2009/0080751 | A1* | 3/2009 | Rasche | A61B 6/032 382/132 |
| 2010/0316184 | A1* | 12/2010 | Iwanczyk | A61B 6/032 250/366 |
| 2011/0211669 | A1* | 9/2011 | Herrmann | G01T 1/249 378/19 |
| 2013/0083887 | A1* | 4/2013 | Li | A61B 6/032 438/73 |
| 2013/0119260 | A1* | 5/2013 | Nakatsugawa | A61B 6/4208 250/366 |
| 2013/0156157 | A1* | 6/2013 | Engel | G21K 1/025 378/62 |
| 2013/0168796 | A1* | 7/2013 | Ikhlef | H10F 30/223 257/E31.124 |
| 2013/0301799 | A1* | 11/2013 | Kang | A61B 6/4241 378/62 |
| 2014/0309518 | A1* | 10/2014 | Sung | A61B 5/055 600/407 |
| 2014/0314196 | A1* | 10/2014 | Zou | A61B 6/032 378/4 |
| 2014/0334600 | A1* | 11/2014 | Lee | A61B 6/4241 250/336.1 |
| 2015/0146849 | A1* | 5/2015 | Kang | A61B 6/4233 378/62 |
| 2017/0212253 | A1* | 7/2017 | Fu | A61B 6/032 |
| 2018/0120455 | A1* | 5/2018 | Eismann | A61B 6/037 |
| 2018/0246229 | A1* | 8/2018 | Preston | G01T 1/20189 |
| 2019/0285758 | A1* | 9/2019 | Yang | G01T 1/1644 |
| 2019/0288026 | A1* | 9/2019 | Von Kaenel | G01N 23/046 |
| 2020/0170592 | A1* | 6/2020 | Bai | A61B 6/025 |

* cited by examiner

RADIATION SENSOR WITH INTEGRATED ELECTRONICS

FIELD

Embodiments of the subject matter disclosed herein relate to computed tomography imaging devices for medical imaging, and more particularly, to radiation detection devices.

BACKGROUND

Computed tomography (CT) imaging devices provide detailed cross-sectional images for diagnosing and treating various conditions. Traditional CT imaging devices rely on radiation sensor arrays that transmit signal readings to external electronics chips. Such sensor arrays have high power consumption requirements and require complex interconnections and are not easily scalable to be used for larger coverage or advanced detectors. Radiation sensor arrays with integrated electronics offer advantages such as reduced connection complexity and scalability.

SUMMARY

An embodiment relates to a computed tomography (CT) imaging system. The CT imaging system includes a detector array configured to detect X-ray projections from a source. The detector array includes a semiconductor sensor array. The semiconductor sensor array includes a plurality of sensors. Each sensor includes a first surface, a second surface, a substrate, and a readout electronics unit. The first surface of the sensor includes a first dopant. The first surface has a high-voltage bias and is configured to receive the X-ray projections. The second surface of the sensor is opposite the first surface and includes a plurality of second regions of a second dopant. The second surface has a low-voltage bias and is configured to collect a plurality of charges from the X-ray projections. The substrate comprises a semiconductor material including the first dopant and is positioned between the first surface and the second surface. The semiconductor material has a resistivity of at least five kiloohm centimeters. The readout electronics unit is positioned on the second surface and between the plurality of sensing regions. The readout electronics unit has a surface area that is less than one percent of a surface area of the second surface.

Another embodiment relates to a system. The system includes a semiconductor sensor array. The semiconductor sensor array includes a plurality of sensors. Each sensor includes a first surface, a second surface, a substrate, and a readout electronics unit. The first surface of the sensor includes a first dopant. The first surface has a high-voltage bias and is configured to receive the X-ray projections. The second surface of the sensor is opposite the first surface and includes a plurality of second regions of a second dopant. The second surface has a low-voltage bias and is configured to collect a plurality of charges from the X-ray projections. The substrate comprises a semiconductor material including the first dopant and is positioned between the first surface and the second surface. The semiconductor material has a resistivity of at least five kiloohm centimeters. The readout electronics unit is positioned on the second surface and between the plurality of sensing regions.

Another embodiment relates to a method for detecting X-ray projections. The method includes receiving the X-ray projections on a first surface of a semiconductor sensor. The method includes transporting charges of the X-ray projections through a substrate. The substrate comprises a semiconductor material having a resistivity of at least five kiloohm centimeters. The method includes collecting the charges by a plurality of sensing regions on a second surface of the semiconductor sensor. The second surface is opposite the first surface. The method includes processing, by a readout electronics unit positioned on the second surface of the semiconductor sensor, the portion of the charges collected by the plurality of sensing regions. The readout electronics unit occupies less than one percent of the second surface of the semiconductor sensor.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

DETAILED DESCRIPTION

Figure 1:
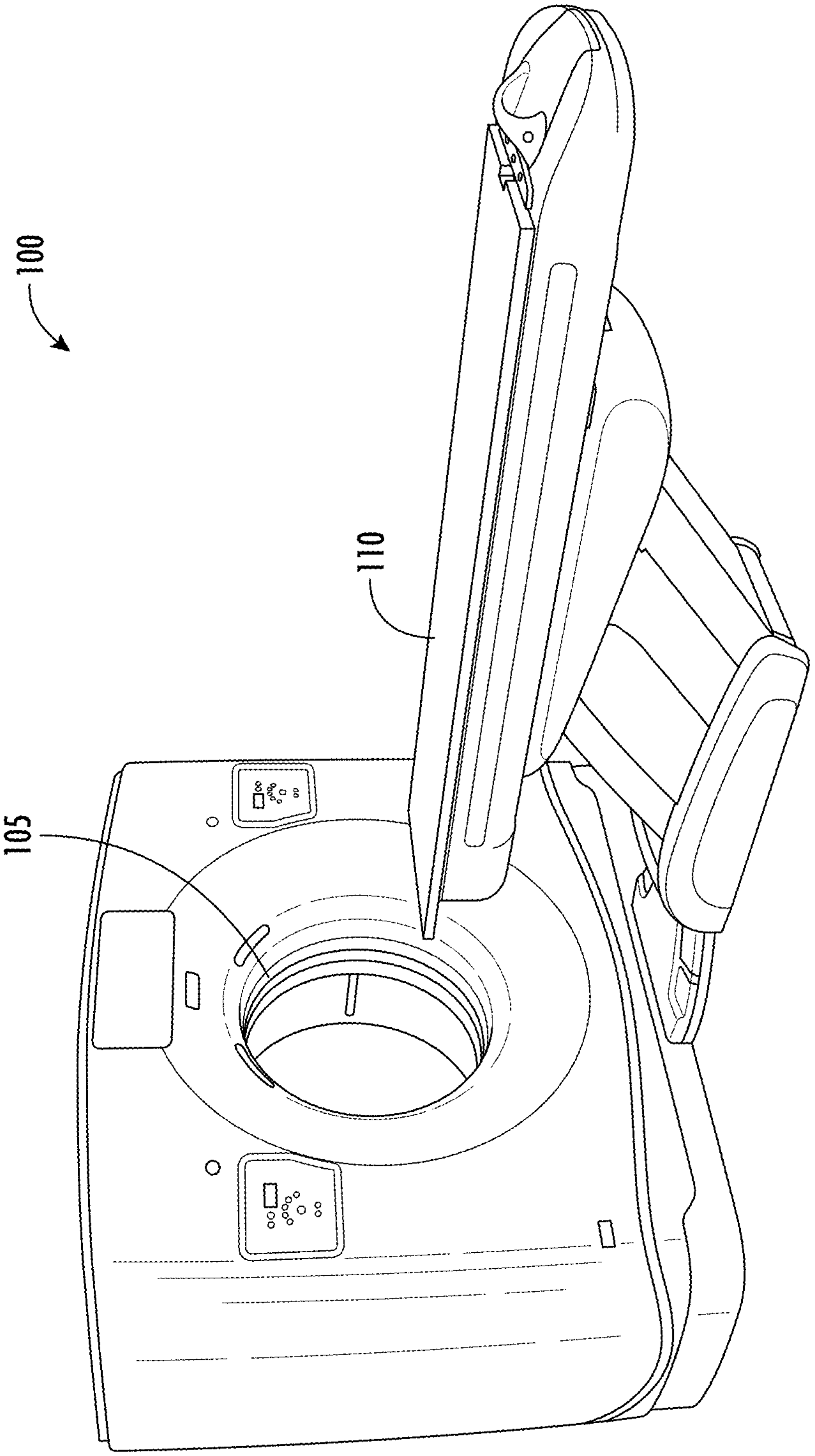
FIG. 1 is a perspective view of a computed tomography (CT) imaging system, according to an example embodiment.

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Referring generally to the figures, systems and methods for detecting X-ray projections during a computed tomography (CT) scan are disclosed. More specifically, the systems and methods described herein include detecting the X-ray projections using a sensor array of radiation sensors. The sensors may be configured with various materials such that they act as P-I-N junctions when an electric field is applied. Each of the sensors may have a first end acting as a contact point to receive the high-voltage X-rays. The charges may pass through a substrate, guided by the electric field, and the photons generated by the X-rays may be collected at a second end. The collected photons may be processed by readout electronics that may be at least partially disposed on the sensor (e.g., monolithic integration).

In existing CT imaging systems, radiation sensors used in photon-counting detector (PCD) arrays utilize a passive pixel structure to transmit detected signals (e.g., the signals must be transmitted across a long trace to the edge of a sensor and transmitted to external circuitry using wired connections). However, such an array structure may not be effective for larger coverage or advanced detectors for various reasons. For example, a larger coverage may require an increased amount of external circuitry, thereby increasing the overall power demand and signal processing complexity of the system. Some newer implementations of radiation sensor arrays utilize monolithic integration, meaning that some of the external readout circuitry is integrated on or within each of the sensors. However, these sensors present new challenges. For example, it may be a challenge to effectively integrate the electronics within the sensor material, due to differences in the material and electrical properties. For example, these sensors may require intermediary doping layers, additional biasing, or other additional components to electrically limit charge entry into the electronics. The additional components may increase manufacturing complexity, increase manufacturing cost, or reduce signal quality. Additionally, it may be challenging to produce high-resolution medical images, as charge sharing may occur between sensing pixels.

The systems and methods described herein, however, provide a technical solution to existing systems by providing a radiation sensor array with integrated electronics. Monolithic integration of the readout electronics is implemented, thereby enabling the sensor array design to be scalable for use in various applications. The sensor array may be made from a semiconductor material with a high resistivity to optimize signal quality as the signals travel towards the sensing regions. The sensor array may also have a front-illuminated or edge-illuminated structure, which eliminates the need to transfer the signals across long traces of the sensors, thereby reducing signal loss and minimizing the complexity of each sensor. Additionally, the sensor array is configured to promote manufacturing efficiency. For example, the materials, dimensions, etc. of each of the sensors is carefully selected such that intermediary structures are not required to effectively integrate the electronics into the sensor array. The sensor array has various features meant to optimize signal quality. For example, the sensing pixels and the readout electronics are strategically sized and positioned on each sensor in a way that reduces signal leakage into the readout electronics. Additional techniques, such as radiation hardening and buried oxide isolation, may be employed to further protect components of each sensor, thereby optimizing quality of the resulting signals.

The implementations described herein address a technical problem by providing enhanced data integration and analysis capabilities, which deliver a particular technical solution that streamlines and refines generation and transmittal of CT images. For example, the systems described herein, including the radiation sensor array, may refine data analysis by promoting efficiency of signals being detected and transferred by the sensors. For example, the radiation sensor array is designed to reduce unintentional photon collection by the readout electronics, thereby increasing the efficiency of signal reading. Additionally, various techniques are employed to simplify the construction of the sensor array, while still ensuring that high quality CT images generated.

The systems described herein may also reduce processing power by performing various processing operations simultaneously, rather than performing a plurality of processing operations individually and consuming unnecessary processing power. For example, the radiation sensor array is configured to both receive the high-voltage X-rays that exit a patient and effectively lower the intensity of the signals such that low-voltage readout electronics can be used within the sensor. Accordingly, no additional processing power is required to attenuate the X-ray signals to be compatible with the readout electronics. Additionally, the low-voltage readout electronics consume less processing power than traditional processing electronics.

Referring to FIG. 1, among others, a CT imaging system 100 is shown. The CT imaging system 100 may be used in a medical environment (e.g., hospitals, clinics, mobile clinics, etc.), for example, by a radiographer, technician, or other clinician certified to perform a CT scan on a patient.

As described herein, the CT imaging system 100 is configured to perform medical imaging using X-ray CT technology. Generally, CT is an imaging technique configured that creates two-dimensional (2D) cross-sectional images or three-dimensional (3D) volumetric images of 3D structures. Such tomographic techniques are particularly useful for non-invasive imaging, such as for security screening, baggage and package examination, manufacturing quality control, and medical evaluation. As a brief overview, when used for medical evaluation, an X-ray CT system generates the cross-sectional or volumetric images of subjects/objects based on X-ray projection measurements. X-rays are omitted from one or more X-ray focal spots, pass through the subject, and are then detected by one or more X-ray detector arrays. This process of X-ray emission and detection is repeated at multiple angles relative to the subject, which results in a set of projections (e.g., views). Then, tomographic reconstruction is performed to generate images from the set of projections. Such a method for performing medical imaging using the CT imaging system 100 is described in greater detail below with reference to FIG. 4.

As shown in FIG. 1, the CT imaging system 100 includes a gantry (e.g., gantry 105) and a patient support structure (e.g., patient support structure 110). According to the embodiment shown in FIG. 1, the CT imaging system 100 is a horizontal system. That is, the gantry 105 is positioned vertically and has an inner volume configured to receive the patient support structure 110 horizontally or substantially horizontally. Prior to an imaging process, a patient may be positioned on the patient support structure 110. The patient support structure 110 may be a table, a gurney (e.g., used for patients who may in an immobile state), a mattress/pad, or a wheelchair, among others. Additional support structures, such as a headrest, an arm support (e.g., handles, arm rests, etc.), a leg support (e.g., leg straps, leg rests, etc.), or other secondary support structures may be included on the patient support structure 110. In some implementations, the CT imaging system 100 is a vertical or substantially vertical system (e.g., a stationary CT (sCT) imaging system, CT imaging systems configured to image a patient in an upright position, etc.). In these instances, the patient support structure 110 may include standing or seated support structures. The gantry 105 may have an inner volume configured to receive at least part of the patient or the patient support structure 110. The gantry 105 may include an imaging unit (e.g., the source 115 and the detector array 120). The imaging unit may include one or more x-ray sources (e.g., single X-ray sources, dual X-ray sources, source arrays, cone-shaped X-ray source, etc.), shown as source 115 in FIG. 2. The imaging unit may include one or more detector arrays (e.g., scintillation detectors, flat-panel detectors (FPDs), photon-counting detectors, etc.), shown as detector array 120 in FIG. 2. The functionality of the gantry 105, including the source 115 and the detector array 120, is described in greater detail herein.

Figure 2:
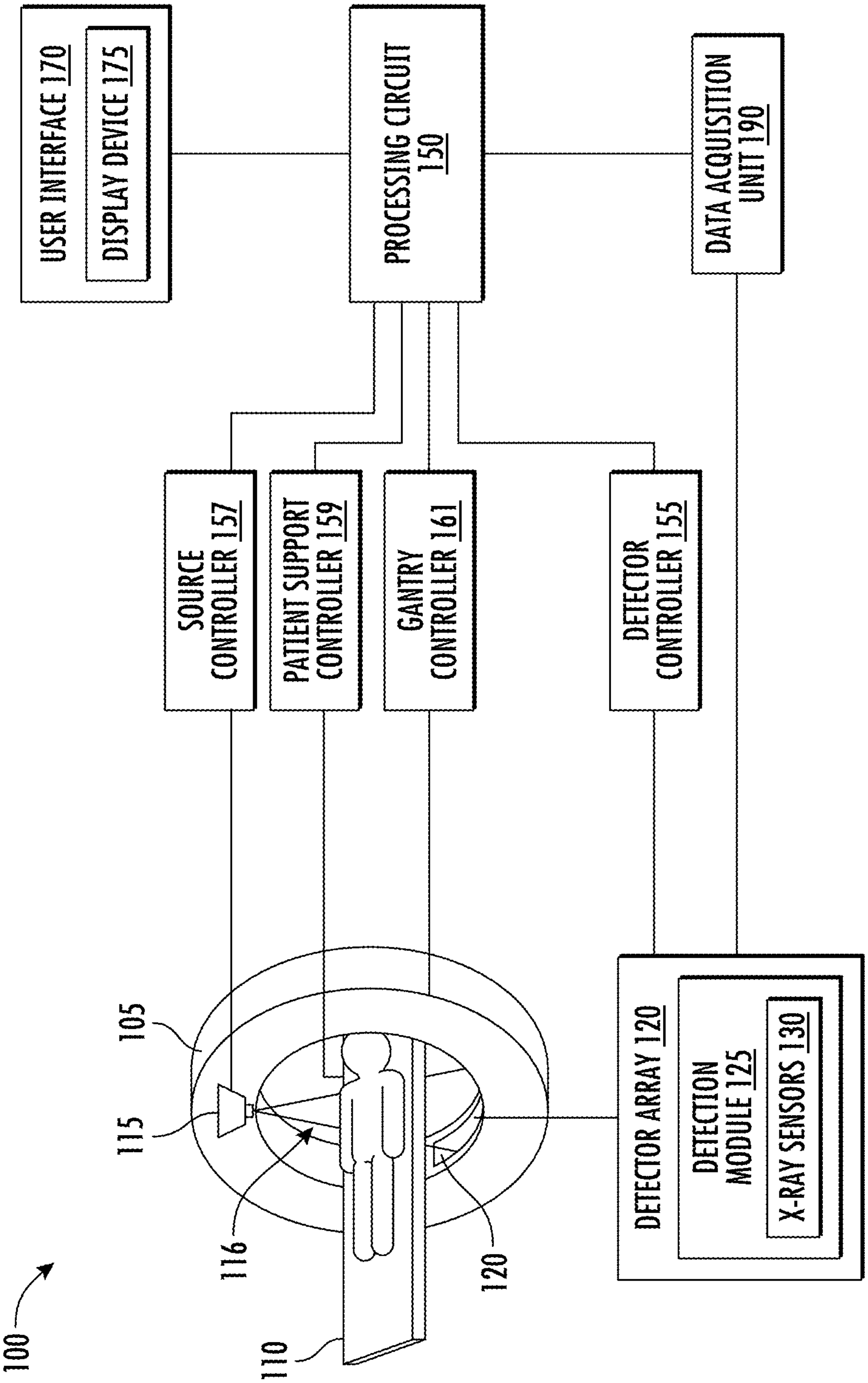
FIG. 2 is a block diagram of the CT imaging system of FIG. 1, according to an example embodiment.

Referring to FIG. 2, a block diagram of the CT imaging system 100 is shown, according to an example embodiment. The CT imaging system 100 may include the gantry 105, including the source 115 and the detector array 120, a processing circuit 150, a detector controller 155, a source controller 157, a patient support controller 159, a gantry controller 161, a data acquisition unit 190, and a user interface 170.

The gantry 105 may include an imaging unit. In some embodiments, the imaging unit refers to the source 115 and the detector array 120. The source 115 may be an X-ray source comprising an electron emitter and an anode. The electron emitter may include, for instance, a thermionic emitter, field emitter or cold cathode (e.g., such as a carbon nano tube), or a dispenser cathode. In some configurations, the electron emitter or the cathode is associated with a single focal spot. The gantry 105 may also include mechanical components to facilitate an imaging process. For example, the gantry 105 may include motors to rotate the imaging unit during the imaging process, such that 2D images corresponding to various angular positions are generated.

In some embodiments, the source 115 is powered using a high-voltage (HV) generator. The source 115 may be connected to the HV generator via one or more HV cables. Furthermore, in some embodiments, the CT imaging system 100 may include a power distribution unit used to convert an external power supply (e.g., from a battery) to a voltage input type required by the source 115, the HV generator, or various control boards (described below).

In some embodiments, a collimator may be positioned proximate to the source 115 (or the one or more focal spots) in order to collimate the outbound X-ray beams (e.g., X-rays 116). In this way, the collimator may be configured to facilitate the source 115 in emitting the X-ray beams in the direction of the detector array 120 (e.g., so the X-ray beams are detected) rather than in other directions where the X-ray beams may be wasted/not detected and possibly cause unnecessary irradiation of tissue or persons. Additionally or alternatively, the collimator (or a second collimator) may be positioned proximate to the detector array 120 in order to collimate the X-ray beam as it exits the object being imaged. In this way, the collimator may be configured to minimize an amount of unwanted X-rays (e.g., scattered radiation, X-rays that did not pass through the object being imaged, etc.) that are received by the detector array 120.

Furthermore, the one or more sources (e.g., the source 115) may include X-ray filters positioned proximate (e.g., in front of) the source 115. In some instances, the X-ray filter may include a flat X-ray filter configured to optimize an X-ray spectrum of the X-rays emitted from the source 115. Additionally or alternatively, the X-ray filter may include a shaped X-ray filter (e.g., a bowtie filter) configured to modulate X-ray intensity as a function of fan angle or cone angle. In this way, the shaped X-ray filter may be configured to optimize the dose profile relative to a patient anatomy. In some embodiments, a plurality of X-ray filters may be used (e.g., when the imaging unit includes multiple sources, the one or more sources include multiple focal spots, etc.).

The detector array 120 may include a crystal or ionizing gas that, when struck by X-ray photons (e.g., emitted by the source 115), produces light or electrical energy that is detected and acquired for generation of medical images during a CT scan. In some embodiments, the detector array 120 may include energy-integrating detectors, which use a scintillator material configured to convert X-rays to visible light combined with photodiodes which are further configured to convert the visible light to an electronic signal. The scintillator material may be portioned into individual blocks (e.g., 1 mm×1 mm×3 mm), and the individual blocks may be separated by optical reflectors. According to such embodiments, the detector array 120 may include a 2D array of detector cells/pixels, each detector cell/pixel including a scintillator block and a photodiode.

Additionally or alternatively, the detector array 120 may be a photon-counting detector. The photon-counting detector may include a material configured to convert X-rays to electron charge clouds, which are then recorded by sensitive electronics. Such a configuration enables the detector array 120 to count individual X-ray photons and determine the approximate energy of each individual X-ray photon. In some embodiments, the detector array 120 may be another one of various detector types or configurations (e.g., flat-panel detectors (FPDs), photodiode arrays, hybrid detectors, etc.).

The detector array 120 may include a detection module 125. The detection module 125 may store and receive instructions for detecting X-ray radiation. In some embodiments, the detection module 125 includes one or more sensor arrays (e.g., sensor array 127) that may be configured to detect and collect radiation signals. In some embodiments, the detector array 120 may be a photon-counting detector (PCD) array. The detection module 125 may include a sensor array 127 with a plurality of sensors (e.g., sensors 130) that are configured to convert X-ray projections into electron-hole pairs and collect the photon charges (e.g., the holes 180). In some embodiments, the detection module 125 may store data collected by the sensors 130 (e.g., photon signals collected by one or more sensing regions 136, processed photon signals processed by an readout electronics unit 138, etc.).

Components of the imaging unit may be controlled via one or more controllers. For example, the source 115 may be controlled by the source controller 157 and the detector array 120 may be controlled by the detector controller 155. The source controller 157 may be configured to control operation of the source 115 and its component. For example, the source controller 157 may control the emission of X-ray radiations being projected by the source 115. The detector controller 155 may be configured to control operation of the detector array 120 and its components. For example, the detector controller 155 may control operation of the detection module 125 (e.g., readout electronic circuitry in a PCD sensor array, etc.).

The gantry 105 may be controlled by the gantry controller 161. For example, the gantry controller 161 may control the movement of the gantry 105. The gantry controller 161 may control one or more operational parameters of the gantry 105, including, but not limited to, a rotational speed, a direction, a position, a power control, and a motor control. In some embodiments, the gantry controller 161 may communicate with the processing circuit 150. For example, the gantry control circuit 160 may transmit control signals to the gantry controller 161. In some embodiments, the gantry controller 161 may be omitted.

The data acquisition unit 190 may be configured to receive signals from the detector array 120 and process the received signals for storage or image reconstruction. In some embodiments, the signals may be processed by the data acquisition unit 190 in real-time to generate reconstructions of the subject within the imaging volume of the gantry 105. In some embodiments, as shown in FIG. 2, the data acquisition unit 190 receives the signals from the detector array 120 and transmits the processed signals to the processing circuit 150. In some embodiments, the data acquisition unit 190 may be a component within the processing circuit 150. In these implementations, the detector array 120 may directly communicate with the processing circuit 150.

Referring still to FIG. 2, the CT imaging system 100 is shown to include a processing circuit 150. The processing circuit 150 may include processing components described in greater detail below with reference to FIG. 3. It should be appreciated that in some embodiments, the functions described herein with reference to the processing circuit 150 may be performed by one or more controllers (e.g., the source controller 157, the patient support controller 159, the gantry controller 161, the detector controller 155, etc.). The one or more controllers may be configured to control operation of the CT imaging system 100 and its components. For example, the source controller 157 is configured to control the source 115. In some embodiments, a system controller can be configured to control operation of the other controllers or other components of the CT imaging system 100 such as the data acquisition unit 190 and the user interface 170.

The CT imaging system 100 may also include a user interface 170. The user interface 170 may be used by a radiographer or other technician to control operation of the CT imaging system 100. For example, the radiographer may use the user interface 170 to control the input of patient data, to change a scanning or display parameter, or to select various other modes, operations, parameters, etc. of the CT imaging system 100. In some embodiments, the user interface 170 may include an off-the-shelf consumer electronic device such as a smartphone, a tablet, a laptop, and so on. For the purposes of this disclosure, the term "off-the-shelf consumer electronic device" is defined to be an electronic device that was designed and developed for general consumer use and one that was not specifically designed for use in a medical environment. In some embodiments, the user interface 170 may be an electronic device that was designed and developed for use in a medical environment. For example, the electronic device may have been specifically designed for use with the CT imaging system 100.

According to some embodiments, the user interface 170 may be physically separate from the rest of the CT imaging system 100 (e.g., the gantry 105, the patient support structure 110, or the processing circuit 150 and other processing components). The user interface 170 may communicate with the processing circuit 150 through a wired connection and/or a wireless protocol, such as Wi-Fi, Bluetooth, wireless local area network (WLAN), near-field communication, and so on. According to some embodiments, the user interface 170 may communicate with the processing circuit 150 through an application programming interface (API).

In some embodiments, the user interface 170 may include physical controls such as one or more of buttons, sliders, a rotary knob, a mouse, a keyboard, a trackball, hard keys linked to specific actions, soft keys that may be configured to control different functions, a microphone configured to receive voice commands to control the CT imaging system 100, and so on. As shown in FIG. 2, the user interface 170 may also include a display device 175. In some embodiments, the display device 175 may be configured to display a graphical user interface (GUI) based on an instruction from the memory 154. The GUI may include user interface icons representing commands and instructions relating to the operation of the CT imaging system 100. The user interface icons of the GUI may be configured such that a user (e.g., the radiographer, technician, etc.) may select a specific user interface icon in order to initiate a specific function controlled by the GUI. For example, various user interface icons may be used to represent windows, menus, buttons, cursors, scroll bars, and so on. That is, the physical controls of the user interface 170 may be included as individual hardware elements, as user interface icons displayed on the display device 175, or a combination of hardware elements and user interface icons.

In some embodiments, the display device 175 may include a touch-sensitive display device or a touch screen. According to such embodiments, the touch screen may be configured to interact with the GUI displayed by the display device 175 such that a user (e.g., the radiographer) can interact with the GUI via the touch screen. The touch screen may be a single-point touch screen that is configured to detect a single contact point at a time, or the touch screen may be configured to detect multi-point gestures involving contact from two or more of a user's fingers at a time. The touch screen may be a resistive touch screen, a capacitive touch screen, or any other type of touch screen that is configured to receive inputs from a stylus or one or more of a user's fingers. According to some embodiments, the touch screen may be an optical touch screen that uses technology such as infrared light or other frequencies of light to detect one or more points of contact initiated by a user. In some embodiments, the touch screen may be incorporated as part of the display device 175 or may be separate from the display device 175. The user interface 170 may also include a proximity sensor configured to detect objects or gestures that are within a predetermined distance (e.g., five feet, six inches, ten centimeters, etc.) of the proximity sensor. In various embodiments, the proximity sensor may be located on the display device 175 or as part of a touch screen that is separate from the display device 175.

Figure 3:
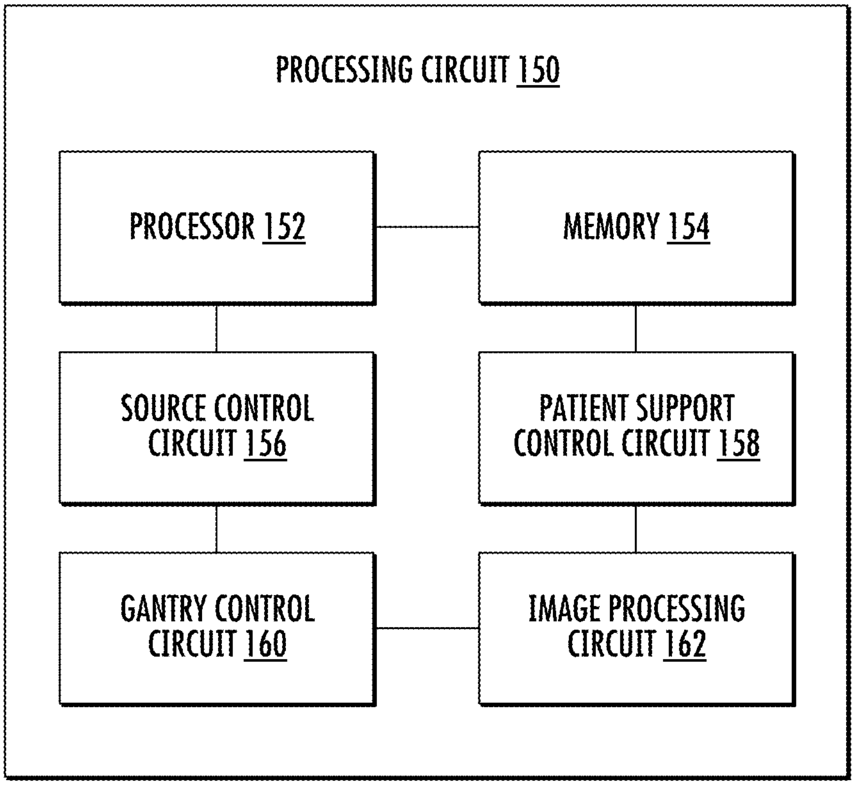
FIG. 3 is a block diagram of a processing circuit used in the CT imaging system of FIG. 1, according to an example embodiment.

Referring to FIG. 3, the processing circuit 150 of the CT imaging system 100 is shown in greater detail. As shown, the processing circuit 150 may include a processor 152, memory 154, a source control circuit 156, a patient support control circuit 158, a gantry control circuit 160, and the imaging processing circuit 162. In this way, the processing circuit 150 may be structured or configured to execute or implement the instructions, commands, or control processes described herein with respect to the processor 152, the memory 154, the source control circuit 156, the patient support control circuit 158, the gantry control circuit 160, and the imaging processing circuit 162. Although shown as components of the processing circuit 150 in FIG. 3, the processor 152, the memory 154, the source control circuit 156, the patient support control circuit 158, the gantry control circuit 160, and the imaging processing circuit 162 may or may not be provided within the same physical structure in an actual implementation.

The processor 152 may include a CPU, a GPU, a microprocessor, a DSP, a general-purpose single- or multi-chip processor, a field-programmable gate array (FPGA), or any other type of processor capable of performing numerical operations. A general-purpose processor may be a microprocessor, or, any conventional processor, or state machine.

A processor also may be implemented as a combination of computing devices, such as a combination of a DSP and a microprocessor, a plurality of microprocessors, one or more microprocessors in conjunction with a DSP core, or any other such configuration. In some embodiments, the processor 152 may be shared by multiple circuits (e.g., the circuits of the processor 152 may include or otherwise share the same processor which, in some example embodiments, may execute instructions stored, or otherwise accessed, via different areas of the memory 154). Additionally or alternatively, the processor 152 may be structured to perform or otherwise execute certain operations independent of one or more co-processors. In some embodiments, two or more processors may be coupled via a bus to enable independent, parallel, pipelined, or multi-threaded instruction execution. All such variations are intended to fall within the scope of the present disclosure.

In some embodiments, the CT imaging system 100 may include multiple processors configured to perform the processing operations/functionality described with reference to processor 152. The processor 152 may also be in electronic communication with a display device (e.g., display device 175) such that the processor 152 may process X-ray projection measurements and generate images to display on the display device 175.

In some embodiments, the memory 154 may store processed volumes of data obtained by the CT imaging system 100 (e.g., X-ray projection measurements received by the detector array 120 or the data acquisition unit 190). For example, the memory 154 may be a hospital picture archiving and communication system (PACS). The memory 154 (e.g., memory, memory unit, storage device, etc.) may include one or more devices (e.g., RAM, ROM, Flash memory, hard disk storage, etc.) for storing data or computer code for completing or facilitating the processes, layers, and modules described in the present application. The memory 154 may be or include tangible, non-transient volatile memory or non-volatile memory. The memory 154 may also include database components, object code components, script components, or any other type of information structure for supporting the activities and information structures described herein.

In some embodiments, the source control circuit 156 is configured to regulate an emission of X-ray radiation from the source 115 toward the detector array 120. More specifically, the source control circuit 156 may be configured to control a timing of X-ray emission such that the X-rays emitted from the source 115 are then detected by the detector array 120 at an opposite side thereof. In some instances, the source control circuit 156 may trigger one or more electron emitters providing X-ray emission from the source 115 at specific intervals to facilitate multiple acquisitions of transmitted X-ray intensity data. Such measurements (e.g., the transmitted X-ray intensity data) may be collected during an imaging sequence performed by the CT imaging system 100.

In some embodiments, the patient support control circuit 158 is configured to position the patient support structure 110 such that objects to be imaged that are positioned thereon/therein are positioned in a plane or volume in which radiation is being emitted (e.g., as controlled by the source control circuit 156). In some implementations, the table control circuit 158 is configured to displace the patient support structure 110 during or between imaging sequences, depending upon an imaging protocol being employed during the CT scan. For example, a patient may be positioned on a table (e.g., the patient support structure 110) prior to an imaging process. Once the patient is properly positioned, the patient support control circuit 158 may horizontally displace the table to an imaging position such that the region of interest (e.g., a pair of lungs for a lung CT scan, etc.) can be imaged. In this instance, the patient support structure 110 may be at least partially received within an inner volume of the gantry 105.

In some embodiments, the gantry control circuit 160 is configured to regulate rotation of the gantry 105 during an imaging process. More specifically, the gantry control circuit 160 may be configured to regulate the rotational speed and timing of the gantry 105 rotation. For example, the gantry control circuit 160 may be configured to rotate the gantry 105 a number of times such that an optimal number of 2D images are acquired. In some embodiments, the gantry control circuit 160 is configured to regulate the operation of the rotation mechanics within the gantry 105. In some embodiments, the gantry control circuit 160 is operably coupled to one or more other control circuits in the CT imaging system 100. For example, the gantry control circuit 160 may communicate with the source control circuit 156 to synchronize rotation of the gantry 105 with the X-ray emissions. As another example, the gantry control circuit 160 may communicate with the data acquisition unit 190 in real-time or near real-time to ensure that the imaging data (e.g., the signals detected by the detector array 120) corresponds to the correct orientation of the source 115 and detector array 120.

The image processing circuit 162 may process acquired CT projection data by various mathematical operations, algorithms, and techniques. For example, conventional filtered back-projection techniques may be used to process and reconstruct data acquired by the CT imaging system 100. Other techniques, such as deep learning processing, and techniques used in conjunction with filtered back-projection may also be employed.

Figure 4:
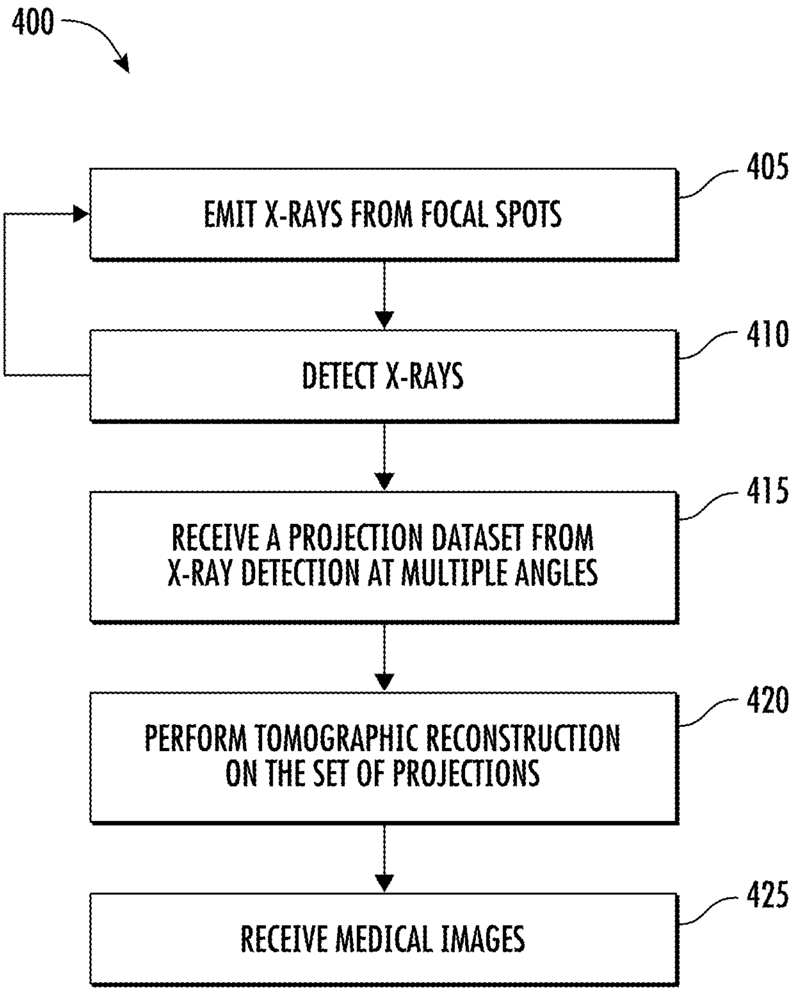
FIG. 4 is an illustration of a method of collecting image data during a CT scan using the CT imaging system of FIG. 1, according to an example embodiment.

Referring to FIG. 4, a flow chart is shown illustrating a method 400 for collecting image data during a CT scan using a CT imaging system. In at least one embodiment, the CT imaging system referred to by method 400 is the CT imaging system 100 described above with reference to FIGS. 1-3, and method 400 may be implemented by the CT imaging system 100. In some embodiments, the method 400 may be implemented as executable instructions in a memory of the CT imaging system 100, such as the memory 154 of FIG. 3.

Prior to initiating the CT scan as described by method 400, the subject of the CT scan (e.g., patient) is positioned, a scan range may be selected, and a reconstruction region may be selected. In some embodiments, an operator of the CT imaging system 100 (e.g., radiographer) may perform such steps manually (e.g., via the user interface 170). Additionally or alternatively, such steps may be performed using one or more cameras or scout scans (e.g., low dose planar x-ray scans) to confirm the patient's position, the scan range, or the reconstruction region.

A scan protocol may also be determined prior to initiating the CT scan. The scan protocol may define various parameters regarding the CT scan such as an X-ray tube voltage, an X-ray tube current, a bowtie selection, a view time, injection parameters, an X-ray tube current modulation, and so on. In some instances, the scan protocol may be manually selected or confirmed by the operator prior to initiating the CT scan. Additionally or alternatively, determination of the scan protocol may be automated using an estimate of patient anatomy (e.g., from cameras, scout scans, etc.) and computing the scan protocol that may yield, for instance, at least one of a high image quality or a low radiation dose from the X-ray emission. In some embodiments, the estimate of the patient anatomy may be configured to suggest the scan range.

At step 405, X-rays are emitted from the focal spot. For example, the focal spot may refer to an area on the anode (e.g., an anode target) on the source 115. When a cathode in the source 115 emits an electron beam, a collision occurs on the focal spot to create the X-rays. In some embodiments, rotating anodes are used to promote distribution of generated heat (e.g., only a small portion of the electron beam is converted into X-rays and the rest is heat).

At step 410, the X-rays emitted from the focal spot at step 405 are detected by the detector array 120. That is, in some embodiments, the X-ray may be detected at a location along the detector array 120 that is opposite a location of the focal spot from which the X-ray is emitted. Therefore, as the gantry 105 and imaging components within the gantry 105 are rotated during the imaging process, the detector array 120 may detect X-rays at a plurality of angular positions.

As shown in FIG. 4, steps 405 and 410 may be repeated in an iterative process such that the X-ray projections are detected at step 410 from multiple projection angles relative to a subject being imaged. For example, the gantry 105 may rotate in between each iteration of steps 405 and 410 such that the projection angles of the X-rays are varied.

At step 415, a projection dataset from X-ray detection at multiple angles (e.g., resulting from the iteration of steps 405 and 410 described above) is received. The projection dataset comprises projection measurements from a multitude of angular positions, or views, of the source 115 and the detector array 120 relative to the patient or object being imaged. More specifically, the projection dataset may include information regarding how much of an X-ray beam is absorbed as the X-ray beam passes through the patient or object being imaged at each of the multitude of angular positions. For example, such information may be used to identify a density or a composition of tissues (e.g., bones, muscles, etc.) or other objects being imaged.

At step 420, tomographic reconstruction is performed on the set of projections received at step 415. In order to correctly interpret the set of projections and perform accurate reconstruction, the CT imaging system 100 may be configured to perform various calibration techniques such as geometric calibration, air and offset calibration, or spectral calibration. As a general overview, tomographic reconstruction refers to a method of mathematically combining each of the projection measurements from the multitude of angular positions included in the projection dataset received at step 415 to create an image of an interior structure of the patient or object being imaged during the CT scan.

Step 420 may include performing any of a variety of tomographic reconstruction techniques, such as filtered back projection, iterative reconstruction, etc. Filtered back projection, for instance, includes filtering the projection dataset to remove high-frequency noise, back-projecting the filtered projection dataset back across the imaging volume at the angle from which each projection measurement was captured, and summing the back-projected projection measurements to produce a 2D image. The 2D image includes pixels representing the tissue density at a point of the object being imaged. For example, because denser materials such as bones absorb more of the X-ray beam than less dense materials such as soft tissue, the denser materials are depicted by brighter pixels at the respective points on the 2D image, while the less dense materials (e.g., where less of the X-ray beam is absorbed) are depicted by darker pixels. Finally, a plurality of the 2D images may be reconstructed to form a 3D image.

At step 425, medical images (e.g., 2D, 3D, etc.) generated during the tomographic reconstruction are received. That is, the 2D images or the 3D image generated at step 420 may be presented to a user (e.g., a radiographer, doctor, technician, patient, etc.) via the display device 175. In some embodiments, where the medical images received at step 425 include a 3D image, the user may view the 3D image according to a plurality of orientations (e.g., axial, coronal, sagittal, etc.). Additionally or alternatively, in some instances, the user may interact with the display device 175 (e.g., using a finger on a touch screen display, using a cursor, etc.) to rotate, zoom in/out of, or otherwise manipulate the view of the 3D image via the display device 175.

FIGS. 5-11, as described in greater detail herein, relate generally to radiation sensors used to detect X-rays in a CT imaging process. As a brief overview, the radiation sensors described herein may be implemented in a detector array (e.g., a photon-counting detector) to detect X-ray signals to be imaged. The sensors may employ monolithic integration methods. That is, at least a portion of the readout electronics required for photon-counting detection may be integrated within the sensor, reducing a number of interconnects between the sensor and readout electronics circuitry. The radiation sensors may be configured to efficiently operate in high radiation environments (e.g., through exposure of high-voltage X-rays) while still performing processing techniques with low levels of power. For example, the radiation sensors may have a high resistivity to ensure that a voltage seen by the readout electronics is low. Additionally, the radiation sensors are configured in a way that the voltage seen at the electronics is lowered without the use of additional sensor components (e.g., additional substrate layers, junctions, etc.). Accordingly, the radiation sensors, as described herein, may optimize the efficiency at which photons can be collected for processing.

As utilized herein, terms such as “doping,” “dopant,” “doped,” and similar terms refer generally to a process of introducing impurities into a material to modify its electrical properties. For example, a “substrate including a dopant,” a “doped substrate”, and a “substrate that has undergone a doping process”, all generally refer to a substrate with said impurities. Types of dopants may include Negative-Type (N-Type) dopants and Positive-Type (P-Type) dopants. N-Type dopants typically include free electrons as majority charge carriers, thereby increasing the conductivity of the material for which the dopant is added to. Conversely, P-type dopants typically have acceptor atoms that create an electron deficiency, which results in a formation of holes, effectively creating positive charge carriers. In some embodiments (e.g., a P-N junction under reverse bias), an electric field will move the electrons of the N-type dopant towards the P-Type dopant. As a result, when electron-hole pairs are generated from an applied voltage, the electrons will be guided to the N-Type dopant and the holes will be guided to the P-Type dopant.

Generally, dopants (e.g., N-Type and P-Type dopants) are added to a semiconductor to create a doped material. P-type dopants generally have less valence electrons than the semiconductor material it is added to. For example, P-type dopants typically have three valence electrons (e.g., group III elements). For example, a P-type material may include, but is not limited to, boron, aluminum, gallium, indium, among other similar elements. N-Type dopants generally have more valence electrons than the semiconductor material it is added to. For example, N-Type dopants typically have five valence elections (e.g., group V elements). Therefore, an N-type material may include phosphorous, arsenic, antinomy, bismuth, etc. The semiconductor material is typically selected based on application. For example, a semiconductor material used in a radiation sensor for a PCD detector in a CT imaging system (e.g., the detector array 120 in the CT imaging system 100) may be required to effectively absorb high-voltage radiation (e.g., X-rays). Some examples of semiconductors that are suitable for a PCD detector include, but are not limited to, cadmium telluride (CdTe), cadmium zinc telluride (CZT), silicon (Si), Gallium Arsenide (GaAs), and amorphous selenium (Se).

When both an N-Type and a P-Type dopant are used together, for example in a semiconductor sensor (e.g., the sensor 130), a P-N junction is formed. As a brief overview, the P-N junction is configured to control the flow of electrical current by creating an electric field within the sensor. For example, a first surface of the sensor may include an N-Type dopant. The first surface having the N-Type dopant, due to its electrical properties, acts as a contact point for X-ray projections. The X-rays may be absorbed by the N-Type dopant (e.g., photoelectric absorption), thereby generating electron-hole pairs. The sensor may include a second surface including a P-Type dopant. In this way, an electric field (e.g., electric field 142) is formed between the surfaces of the sensor. The electric field may extend through a substrate, which may be disposed between the surfaces of the sensor. In some embodiments, the substrate may be lightly doped with an N-Type dopant (e.g., having a lower concentration of the N-Type dopant as the first surface). In this way, the electron-hole pairs flowing through the substrate may be properly separated. For example, the electron-hole pairs may separate into individual electrons and electron holes (e.g., holes). As the first surface has more negative charge carriers than the substrate (e.g., due to the concentration of the N-Type dopant), the electrons will be guided to the first surface. Similarly, because of the electrical properties of the substrate, the holes will be guided to the P-Type dopant (e.g., the second surface). In certain implementations, for example in a PCD array, the holes are collected (e.g., on the second surface), which are then processed to create medical images.

As utilized herein, the terms “high-voltage bias” and “low-voltage bias” and similar terms refer generally to the electrical properties of objects or components for which the terms are used to describe. For example, a surface of a sensor may be described to have a high-voltage bias. In this instance, it should be understood that the surface may contain a metal contact point, which enables the surface to interact with high-voltage X-ray emissions. When the X-ray emissions are absorbed by the surface, a high-voltage bias is created on the surface. Conversely, a surface opposite the high-voltage contact may be described to have a low-voltage bias. For example, the surface opposite from the high-voltage contact may have a low-voltage bias (e.g., does not have an applied voltage). The potential difference between the high and low voltage surfaces creates an electric field between the surfaces (e.g., through a substrate).

Figure 5:
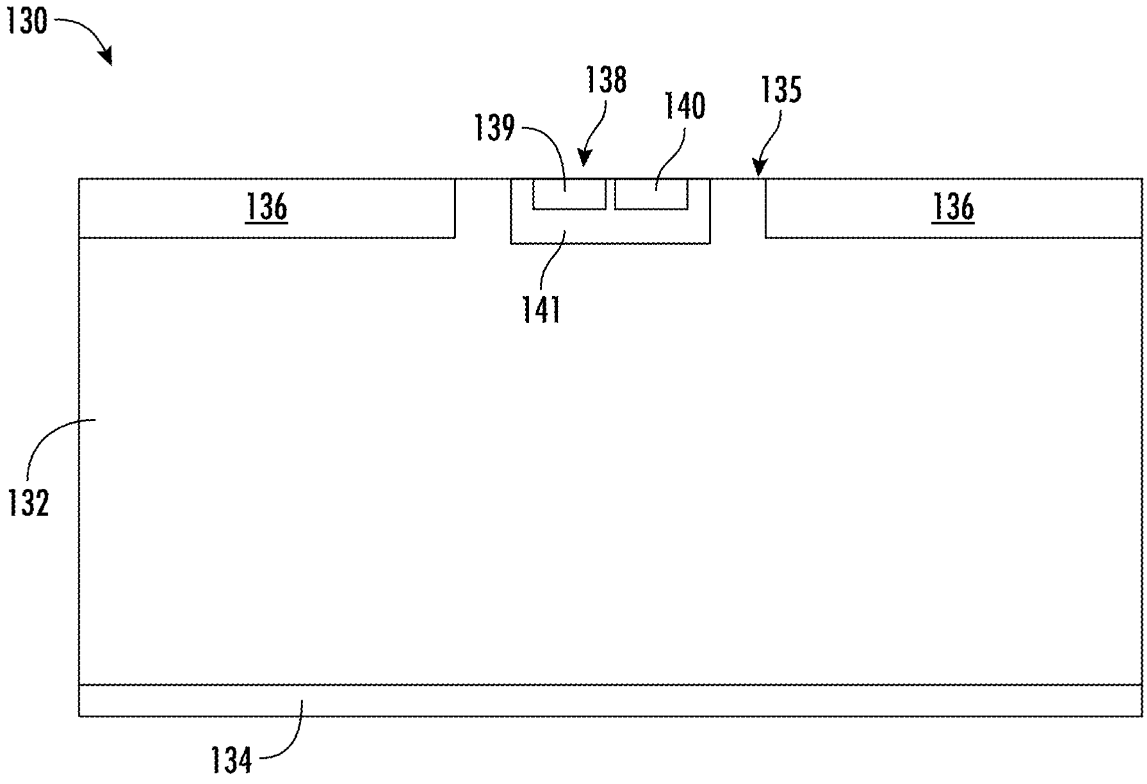
FIG. 5 is a schematic illustration of a radiation sensor used in the CT imaging system of FIG. 1, according to a top view, according to an example embodiment.

Referring now to FIG. 5, among others, a schematic illustration of a radiation sensor (e.g., sensor 130) is shown, according to an example embodiment. FIG. 5 depicts a cross-sectional view of the sensor 130. The sensor 130 may be used to collect the signals used to generate the medical images described above as being collected by the CT imaging system 100. The sensor 130 may be one of a plurality of sensors in a radiation sensing system, such as the detection module 125. In some embodiments, the sensor 130 is configured for use in the detector array 120 when the detector array 120 is a photon-counting detector (PCD).

In some embodiments, such as in FIG. 5, a first surface of the sensor 130 (e.g., first surface 134) is configured to receive the X-ray projections as they exit the object/subject being imaged. For example, the first surface 134 may be or include a region of a material that includes a field-activated dopant (e.g., an N-Type dopant). When a high voltage is applied to the sensor 130 (e.g., via the HV generator), the field-activated dopant is ionized and the first surface 134 becomes high-voltage biased. In some embodiments, the first surface 134 also includes a metal (e.g., a thin metal sheet, the surface impregnated with metal particles, etc.) which may act as an electrical contact for the X-rays. Such metals may have a high conductivity (e.g., gold, platinum, titanium, aluminum, etc.). Additionally, the first surface 134 may be configured to collect electrons as they flow through an electric field, as shown and described in FIG. 7.

Figure 7:
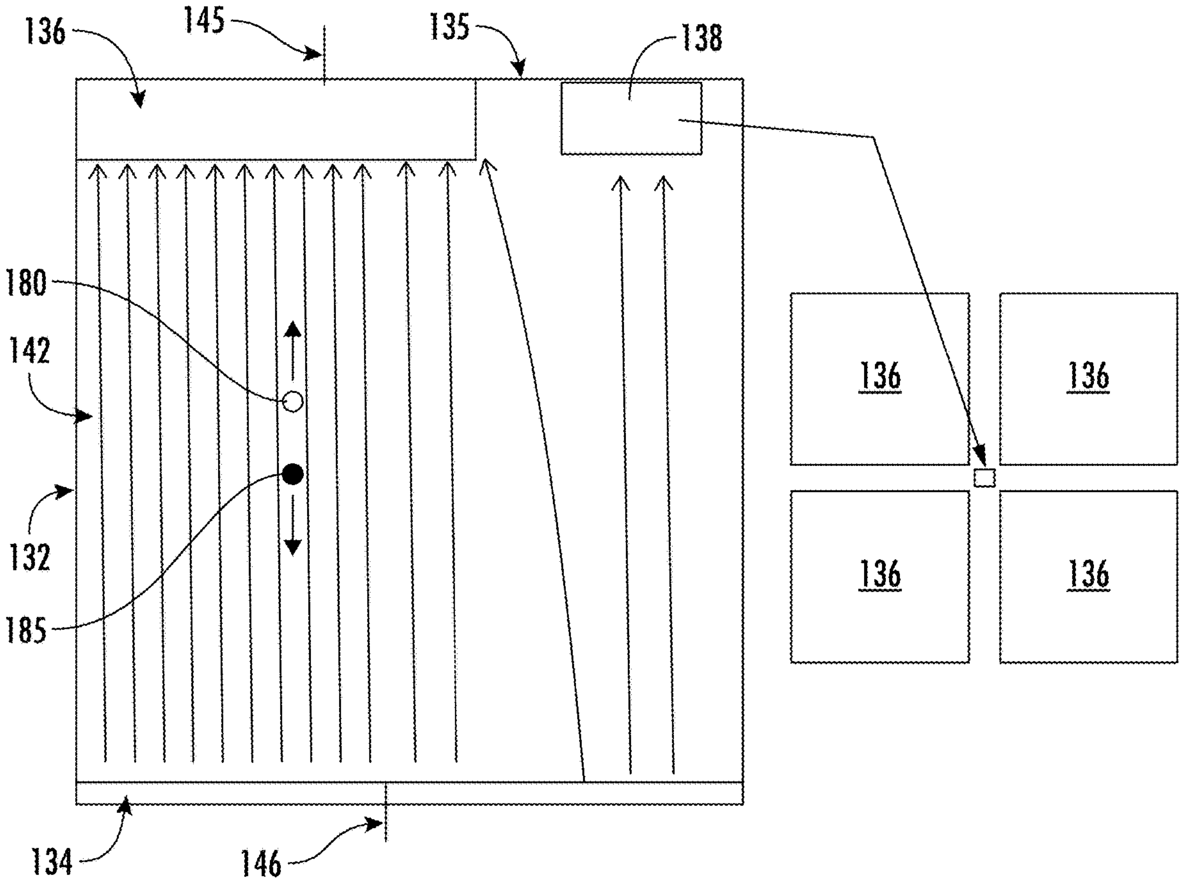
FIG. 7 is a schematic illustration of a radiation sensor used in the CT imaging system of FIG. 1 according to an example embodiment.

As shown in FIG. 5, a second surface of the sensor 130 (e.g., second surface 135) is disposed opposite the first surface 134. In some embodiments, at least part of the second surface 135 is configured to collect charges created from the X-rays. For example, one or more sensing regions (e.g., sensing regions 136) may be disposed on the second surface 135. The sensing regions 136 may be sensing pixels that include a material with a collector dopant (e.g., a semiconductor doped with a P-Type dopant). Through the electric field, the sensing regions 136 may attract or collect holes generated by the X-rays. FIG. 7 illustrates the charges being collected by the sensing regions 136 in greater detail. In some embodiments, the sensing regions 136 have a surface width of at least fifty micrometers. Such a width reduces the likelihood that the charges are collected inadvertently by another region of the sensor 130.

In some embodiments, the surfaces may be coupled by a substrate. As shown in FIG. 5, the substrate 132 is positioned between the first surface 134 and the second surface 135. The substrate 132 may be of a material including the first dopant. In certain implementations, the substrate 132 has a lower concentration of the first dopant than the first surface 134, such to allow proper separation and movement of the electron-hole pairs. The material of the substrate 132 may be chosen based on the resistivity of the material. For example, in some embodiments, the substrate 132 may be made from a semiconductor having a have a resistivity of at least five kiloohm centimeters. Such a resistivity of the semiconductor material may be achieved by the doping concentration (e.g., concentration of N-Type dopants). Such a resistivity may minimize leakage current, thereby improving the quality of the resulting medical images. The substrate 132 may have a different resistivity based on the application (e.g., the resistivity requirements may vary based on device size, operating environment, etc.).

In some embodiments, the second surface 135 includes a readout electronics unit 138. The readout electronics unit 138 may be configured to receive and process the charges collected by the sensing regions 136. As shown in FIG. 5, the readout electronics unit 138 is disposed on the second surface 135 and between the sensing regions 136. In some embodiments, the readout electronics unit 138 covers a minimal surface area of the sensor 130. For example, in certain implementations, the area of the readout electronics unit 138 may be less than one percent of the area of the second surface 135. As another example, the readout electronics unit 138 may have a surface area of around 10 by 10 micrometers.

Still referring to FIG. 5, the readout electronics unit 138 may include, or be disposed in, a region (e.g. P-well, or region 141). In some embodiments, the region 141 may include the same dopant as the sensing regions 136. This configuration of the region 141 allows the readout electronics unit 138 to receive and process the holes 180 collected by the sensing regions 136. Due to the similar material characteristics of the sensing regions 136 and the readout electronics unit 138, the readout electronics unit 138 must be configured to minimize the likelihood of holes 180 being unintentionally collected by the readout electronics unit 138 (e.g., instead of the sensing regions 136). Therefore, in some embodiments, the size of the sensor components may be selected to reduce the likelihood of signal leakage into the electronics. For example, as the readout electronics unit 138 only occupies about one percent of the area of the second surface 135, the likelihood that a hole 180 is guided to the readout electronics unit 138 is significantly reduced. Additionally, as the sensing regions 136 have a large size relative to traditional semiconductor radiation sensors (e.g., at least 50 micrometers in width), the majority of the area of the second surface 135 is occupied by the sensing regions 136. Thus, there is an increased likelihood that the holes 180 are guided to the sensing regions 136, rather than the readout electronics unit 138. Accordingly, the readout electronics unit 138 may optimize the quality of medical images produced by an imaging process, as the detection of X-rays is more precise.

The readout electronics unit 138 may include readout electronics configured to process signals generated by the detection of photons (e.g., holes 180). The readout electronics may be or include one or more Application-Specific Integrated Circuits (ASICs), N-Type Metal-Oxide-Semiconductors (NMOS), P-Type Metal-Oxide-Semiconductors (PMOS), Charge-Sensitive Preamplifiers (CSAs), Analog-to-Digital Converters (ADCs), Voltage Regulators, Field-Programmable Gate-Arrays (FPGAs), comparators, multiplexers or demultiplexers, or other circuitry required for signal processing. The readout electronics for a PCD sensor are typically low-voltage electronics (e.g., electronics that operate efficiently at low voltages). In detail, the components used to detect the photon signals (e.g., from the sensing regions 136) are very compact (e.g., sub-micron technology). Sub-micron electronics, for example, minimize the distance between the sensing regions 136 and the readout electronics unit 138, thereby optimizing photon collection. Additionally, such compact electronics optimize signal processing speed and detection sensitivity, among other signal processing advantages. Such components require low-voltage operation (less than 5 V, less than 3.3 V, less than 1.2 V, etc.).

In some embodiments, Complementary Metal-Oxide-Semiconductor (CMOS) circuitry is used to process the photon signals. In general, CMOS circuitry (including NMOS and PMOS) operates under low-voltage levels. To enable CMOS circuitry operation in the detection module 125, the readout electronics unit 138 may include a P-well 139 (e.g., a region doped with a P-type substrate) and an N-well 140 (e.g., a region doped with an N-type substrate). The P-well 139 may serve as an environment for the NMOS transistors. For example, the contrasting electrical properties of the P-well 139 and the NMOS transistors may promote electrical isolation, and therefore optimal operation, of the NMOS transistors. Similarly, the N-well 140 may serve as an environment that enables optimal operation of the PMOS transistors.

Typically, low-voltage electronics are not suitable to operate in environments with high levels of ionizing radiation (e.g., X-rays). Therefore, in some embodiments, components of the readout electronics unit 138 (e.g., the readout electronics) may be configured to operate when exposed to high levels of radiation. For example, the readout electronics (e.g., the NMOS transistors, the PMOS transistors, and other electronics) may be radiation-hardened. The readout electronics may be radiation-hardened using one or more various methods, including, but not limited to, treatment with gate oxides, annealing steps, and insulation steps. Implementation of radiation-hardened electronics may be advantageous for many reasons, such as minimizing degradation of the electronics and enabling low-power operation of the electronics. Further, the material requirements for the sensor 130 may be reduced (e.g., reducing the necessity for additional substrate layers, P-N junctions, or otherwise reducing the radiation exposed to the electronics).

The detection module 125 may perform various crucial imaging processing functions, thereby reducing the computational requirements of the processing circuit 150 (or other computational components of the CT imaging system 100). For example, the readout electronics unit 138 may process the signals generated by the collected photons (e.g., the holes 180). Such processing may include signal conditioning (e.g., reducing noise, optimizing pulse shapes, etc.), Analog-to-Digital Conversion (ADC), spectral resolution (e.g., sorting photon signals into "energy bins" based on their intensity), calibration, error correction, and various other processing functions.

Figure 6:
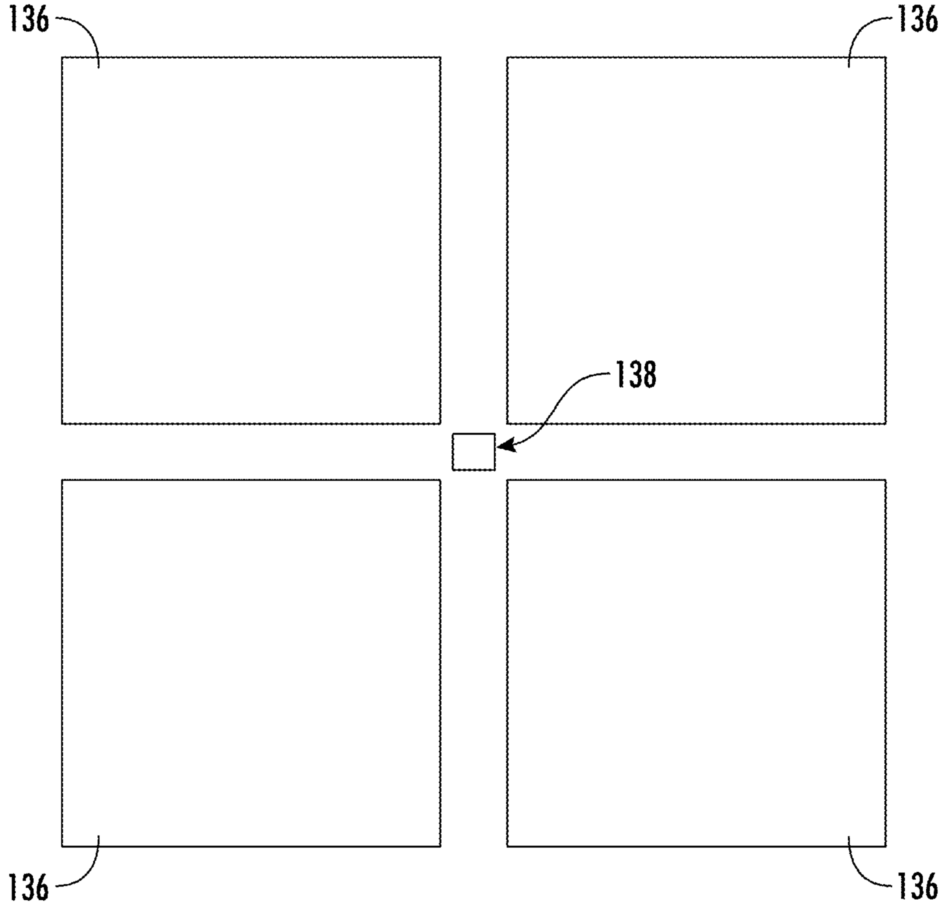
FIG. 6 is a schematic illustration of a radiation sensor used in the CT imaging system of FIG. 1, according to an example embodiment.

Referring now to FIG. 6, among others, a schematic illustration of the sensor 130 is shown, according to an example embodiment. More specifically, a top view of the sensor 130 is depicted. The top of the sensor 130 refers to the second surface 135. In some embodiments, the second surface 135 includes four sensing regions 136 and one readout electronics unit 138. In this implementation, the readout electronics unit 138 may be positioned on an area of the second surface 135 that includes a corner from each of the four sensing regions 136. Such a configuration may reduce signal leakage seen by the readout electronics unit 138. For example, about 99 percent of the area of the second surface 135 that can receive a hole 180 is occupied by a sensing region 136. Additionally, this configuration minimizes the distance between the sensing regions 136 and the readout electronics unit 138, thereby optimizing charge transfer, and consequentially optimizing image quality. In some embodiments, techniques, such as buried oxide isolation techniques, may be used to further reduce signal leakage and unwanted signal coupling. For example, a buried-oxide (BOX) layer may be added as a resistive layer to prevent unwanted signals or charges from entering the readout electronics unit 138. The sensor 130 may be configured with a different number of components than shown in FIG. 6. For example, the sensor 130 may include less than or greater than four of the sensing regions 136, and greater than one readout electronics unit 138.

Referring now to FIG. 7, among others, a schematic illustration (e.g., a cross section view) of the sensor 130 having an applied electric field (e.g., electric field 142) is shown, according to an example embodiment. The electric field 142 applied through the sensor may be generated when a high voltage (e.g., the X-rays 116) contacts the first surface 134, shown as a high-voltage end 146. In some examples, the high-voltage end may have a voltage as high as 250 V. Accordingly, the opposite end has a low-voltage bias, shown as low-voltage end 145. In some examples, the low-voltage end 145 may have a voltage as low as 0 V. The electric field 142 may extend through the entire substrate 132 (e.g., extending from the first surface 134 to the second surface 135). As the X-rays 116 are received and absorbed by the first surface 134, electron-hole pairs are generated. The electron-hole pairs may be separated as they flow through the substrate. For example, each electron-hole pair may separate into an individual hole 180 and electron 185. The electric field 142 may then guide the hole 180 and the electron 185 accordingly. For example, the electron 185 may be guided towards the first surface 134 and the hole 180 may be guided towards the second surface 135 (e.g., specifically the portions of the second surface 135 having the second dopant). Shown in FIG. 7, the hole 180 is guided toward the second surface 135 to be collected by the sensing region 136. Once received by the sensing region 136, the hole 180 is transmitted to the readout electronics unit 138 to be processed.

In some embodiments, such as the sensor 130 depicted in FIG. 7, the sensors 130 may be front-illuminated sensors (e.g., or sensors of a front-illuminated sensor array). In this implementation, the charges generated by the X-rays 116 may typically follow the shortest path from the entry point to the collection point. For example, the X-rays 116 may enter the sensor 130 through the first surface 134 and travel across the substrate 132 to reach the sensing regions 136. In some embodiments, the sensor 130 or the sensor array 127 has an edge illuminated structure, described in further detail in FIG. 9.

Figure 8:
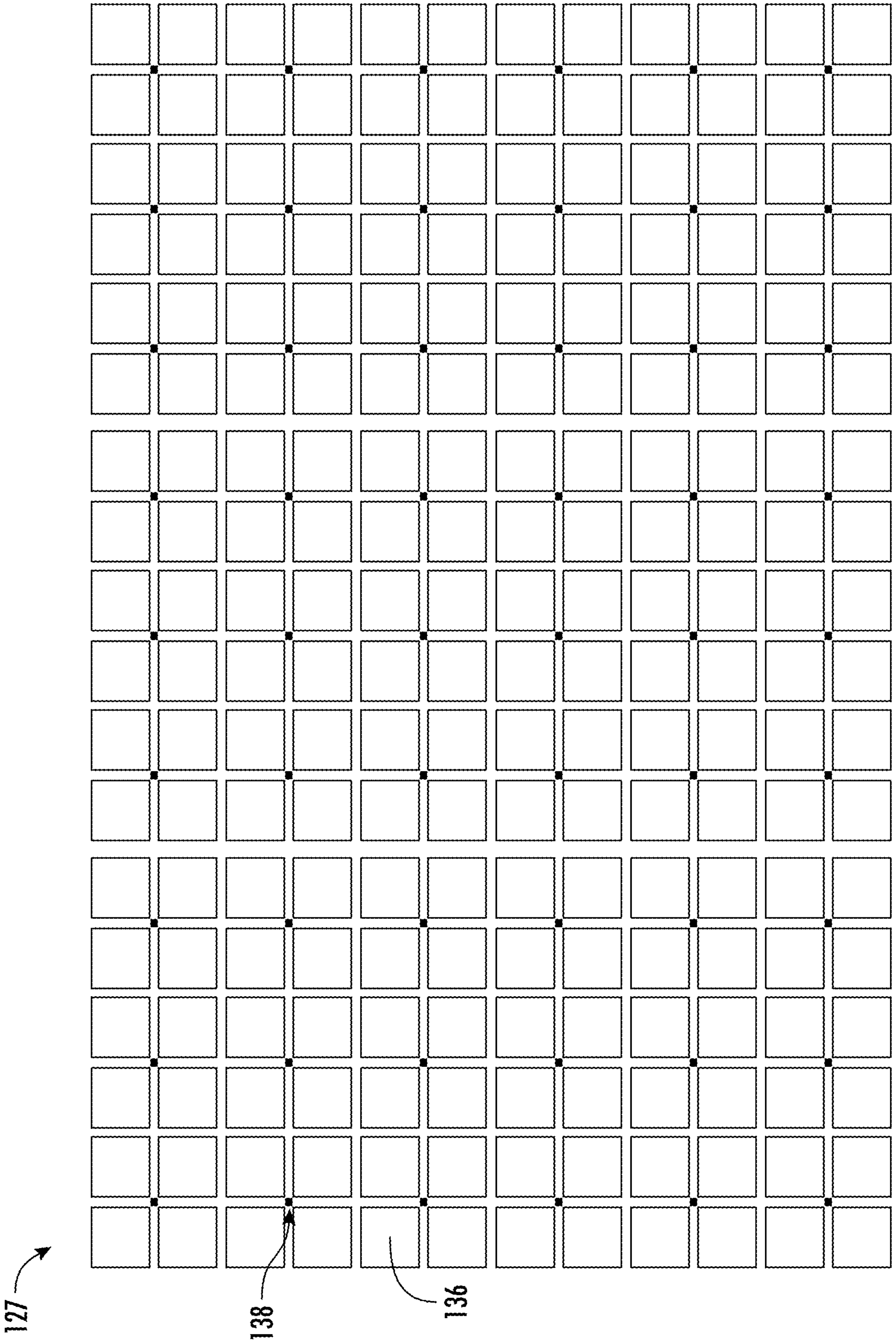
FIG. 8 is a schematic illustration of a sensor array used in the CT imaging system of FIG. 1, according to an example embodiment.

Referring now to FIG. 8, a sensor array (e.g., sensor array 127) is shown, according to an example embodiment. The sensor array 127 may refer to an array of a plurality of sensors 130 (e.g., having a plurality of sensing regions 136 and readout electronics units 138). The sensor array 127 may include a large number of sensors 130 (e.g., typically tens of thousands of sensors). In some embodiments, each sensor 130 in the sensor array 127 includes four sensing regions 136 and a respective readout electronics unit 138, forming a readout electronics area, to process the photons collected by the four sensing regions 136. In some embodiments, the sensor array 127 may be positioned on or within the detector array 120. In some embodiments, a plurality of sensor arrays 127 may be positioned on or within the detector array 120.

Figure 9:
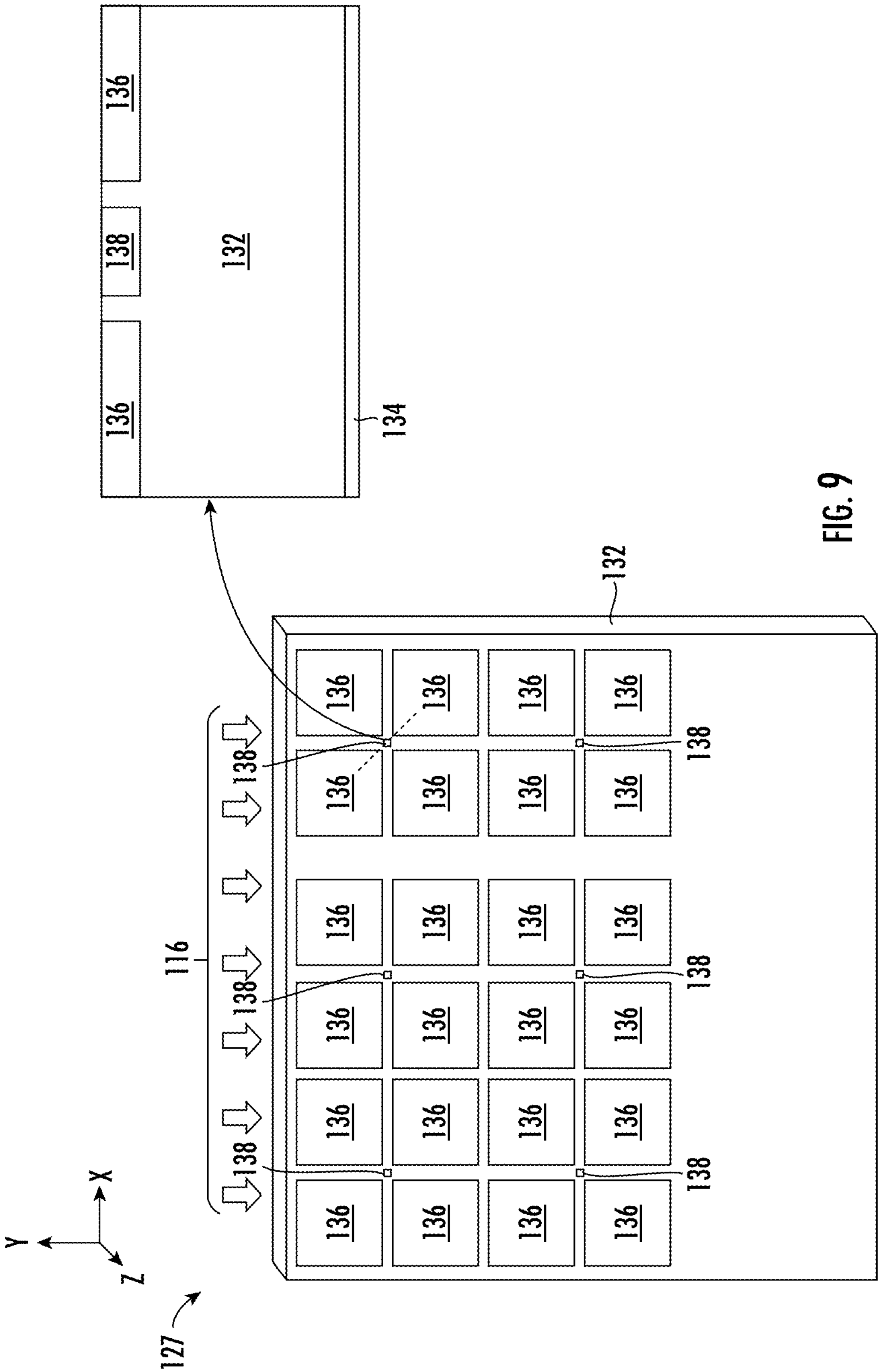
FIG. 9 is a schematic illustration of a sensor array used in the CT imaging system of FIG. 1, according to an example embodiment.

Referring now to FIG. 9, the sensor array 127 may be an edge-illuminated sensor array, in some embodiments. As illustrated, the X-rays 116 may enter the sensor array 127 at an edge of the entire sensor array 127. The edge may correspond to the first surface 134 of the sensor array 127, as the first surface 134 is configured as a contact point for the X-rays 116. The charges from the X-rays 116 then move through the substrate 132 to be collected by the sensing regions 136. In the edge-illuminated structure, the interaction path for the X-rays 116 is increased (e.g., in comparison to the front-illuminated structure), thereby increasing X-ray absorption and enhancing the sensitivity of the sensor 130. Additionally, the large size of the sensing regions 136 (e.g., relative to traditional radiation sensor pixels) enhances the performance of the edge-illuminated sensor array 127 by providing a greater area for charge collection.

Figure 10:
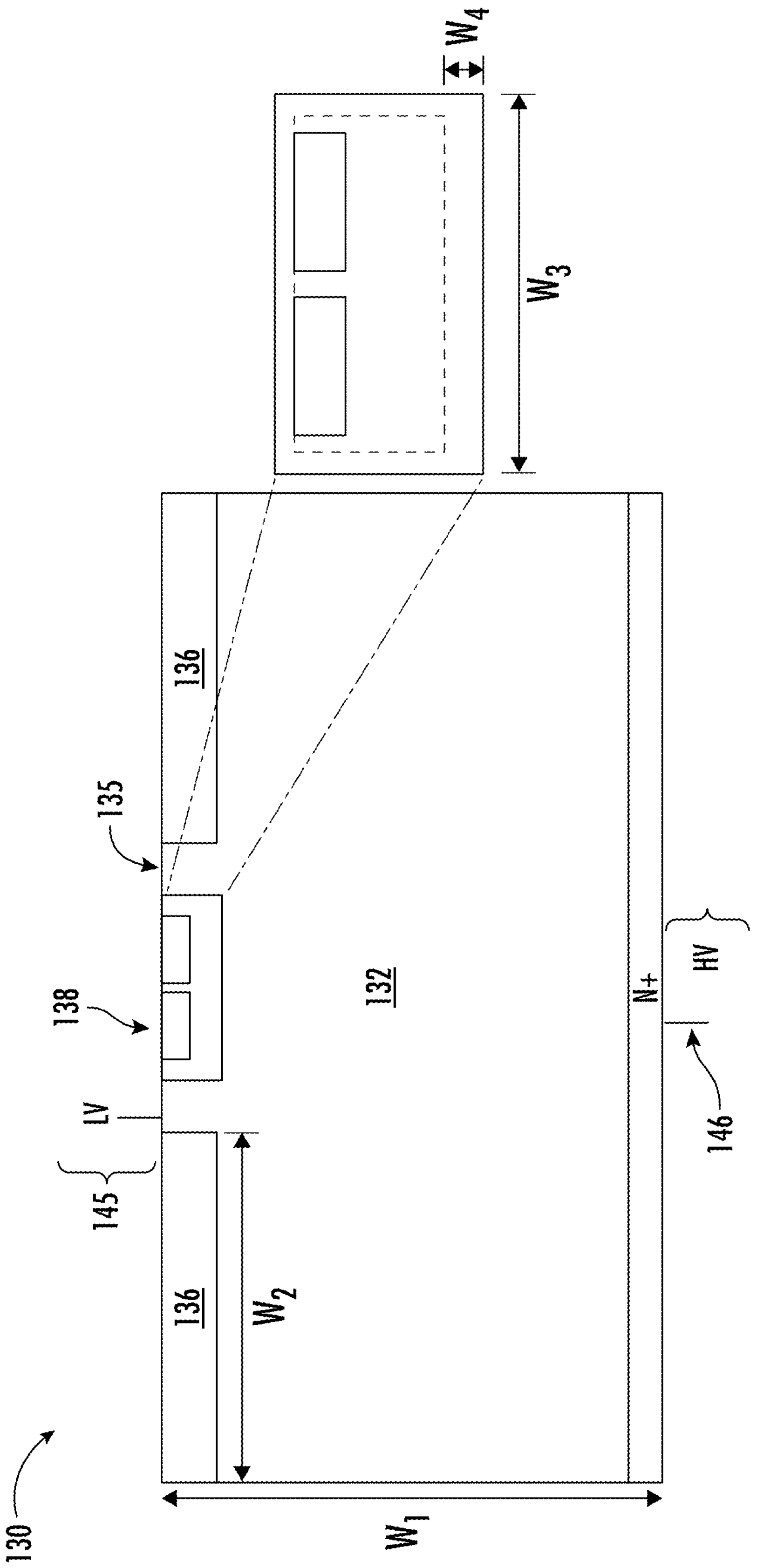
FIG. 10 is a schematic illustration of a radiation sensor used in the CT imaging system of FIG. 1 according to an example embodiment.

Referring now to FIG. 10, a schematic illustration (e.g., a cross section) of the sensor 130, including defined parameters, is shown, according to an example embodiment. In the illustrated embodiment, one or more parameters are predetermined. For example, the width/depth $W_1$ of the sensor 130 may be 650 micrometers (e.g., the width of a commonly-used silicon wafer). Additionally, the surface width $W_2$ of the sensing regions 136 is at least fifty micrometers, and the surface width $W_3$ of the readout electronics unit is 10 micrometers or less. Additionally, the dopant concentration number of the various doped regions may be known (e.g., may be determined during the doping process). In this embodiment the acceptor doping concentration of the P-well (e.g., the region 141) is known to be $1.00\times10^{15}$ acceptor charges (e.g., number of holes available for conduction) per cubic centimeter. The donor doping concentration of the N-type material (e.g., the first surface 134 and the substrate 132) is known to be $4.40\times10^{15}$ donor charges (e.g., number of electrons available for conduction) per cubic centimeter. Accordingly, the width of the depletion region $W_4$ extending into the P-well can be calculated, using the equation shown below. In some examples, the width of the depletion region $W_4$ does not exceed 0.3 micrometers. In at least one embodiment, the width $W_4$ of the depletion region extending into the P-well is determined to be 0.286 μm. Such a result suggests sufficient operation of the sensor 130, as the depletion region will not completely deplete the P-well. For example, it is necessary that the P-well region does not get fully depleted when a voltage is applied to the sensor because operation of the transistors (e.g., the NMOS and PMOS transistors) are reliant on the electrical isolation provided by their conductive regions (e.g., the N-well and P-well). Where $N_A$ and $N_D$ represent the acceptor doping concentration and the donor doping concentration respectively, and $x_N$ and $x_P$ represent the widths of the depletion region extending into the N-type material and the P-well respectively, $x_P$ can be calculated using the following equation:

$$N_A x_P = N_D x_N$$

The parameters of the sensor 130, as illustrated in FIG. 10, may be implemented for optimal sensor operation. For example, the maximum electric field of the junction (e.g., the intensity of the electric field at the first surface 134) may be determined using the equation shown below. The parameters of the sensor 130 may be considered optimal when it is determined that the maximum electric field at the first surface 134 is below the breakdown field of the semiconductor material. In this embodiment, the sensor 130 comprises a silicon material, having a breakdown field of 250 kV/cm. In this embodiment, the maximum electric field is calculated and determined to be 6.01 kV/cm, which is well within the breakdown field. Where $E_{max}$ represents the maximum electric field, q represents the elementary charge of a proton or electron (e.g., $1.602\times 10^{-19}$ C), $\epsilon$ is the permittivity of the material (e.g., $1.04\times10^{-12}$ F/m for silicon), $V_0$ is reverse bias voltage, such as the voltage seen by the first surface 134 (e.g., 250 V), and $N_A$ and $N_D$ are the acceptor doping concentration and the donor doping concentration, respectively, $E_{max}$ can be calculated using the following equation:

$$E_{max} = -\sqrt{\left(\frac{2q}{\epsilon}\right)\times\left(\frac{V_0}{\frac{1}{N_A}+\frac{1}{N_D}}\right)}$$

Figure 11:
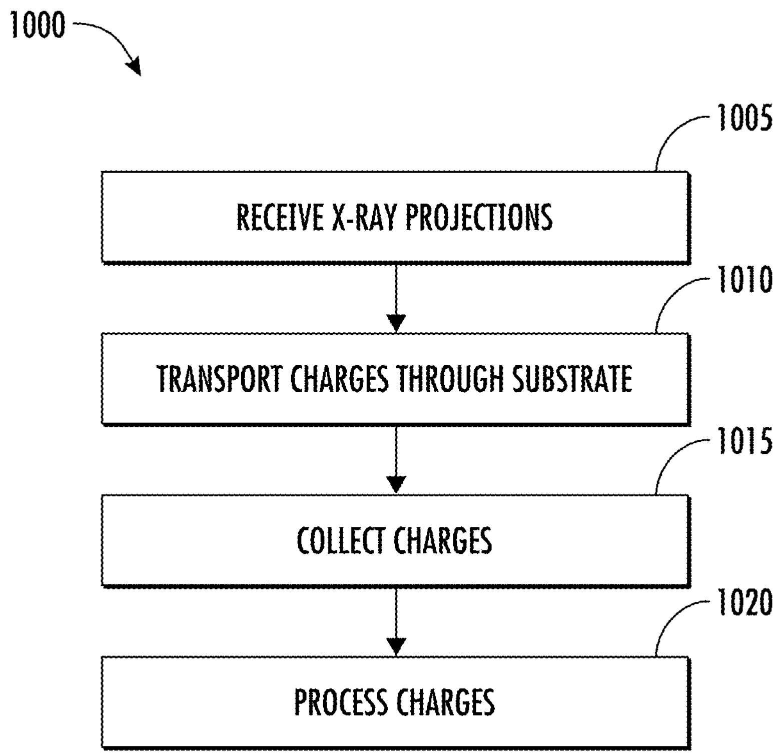
FIG. 11 is an illustration of a method of detecting X-ray projections with the CT imaging system of FIG. 1, according to an example embodiment.

Referring now to FIG. 11, a flow chart is shown illustrating a method 1000 for detecting radiation during an imaging process. In at least one embodiment, the components referred to by method 1000, such as the sensors, are the components of the CT imaging system 100 described above with reference to FIGS. 1-3, and the method 1000 may be implemented, at least in part, by the CT imaging system 100. In at least one embodiment, the sensor referred to by the method 1000 is a sensor described by the sensor 130 or another detection sensor within the detection module 125, described above with reference to FIGS. 5-10, and the method 1000 may be implemented, at least in part, by at least one of the sensors described above. In some embodiments, the method 1000 may be implemented, at least in part, as executable instructions in a memory of the CT imaging system 100, such as the memory 154 of FIG. 3. Multiple sensors may implement the method 1000 simultaneously during an imaging process. Additionally, the method 1000 may complete multiple iterations as the detector array 120 detects X-rays at a plurality of angular positions.

At step 1005, X-ray projections may be received. For example, X-ray projections emitted from a source (e.g., the source 115) may be received by a first surface of a sensor (e.g., the first surface 134 of the sensor 130). The first surface 134 may have a high-voltage bias (e.g., from the X-ray projections). Accordingly, the first surface 134 is configured to receive and absorb the X-rays, creating electron-hole pairs.

At step 1010, charges may be transported through a substrate. For example, a substrate (e.g., the substrate 132) may be positioned between the first surface 134 and a second surface (e.g., second surface 135). An applied electric field may extend through the substrate 132. Due to the electrical properties of the first surface 134, the second surface 135, and the substrate 132 (e.g., doping concentrations), the electron-hole pairs may separate into holes 180 and electrons 185. The holes 180 may then be guided through the substrate 132 towards the sensing regions 136 and the electrons 185 may be guided towards the first surface 134.

At step 1015, the charges may be collected. For example, a second surface of the sensor (e.g., the second surface 135) may include a plurality of sensing regions 136. The sensing regions 136 may be configured to collect the photons (e.g., the holes 180). For example, the sensing regions 136 may have include a P-Type dopant, which, in the low-voltage bias state, may collect the holes 180.

At step 1020, the charges may be processed. For example, the second surface 135 may include readout electronics (e.g., the readout electronics unit 138). The readout electronics unit 138 may receive photon signals from the sensing regions 136. The readout electronics unit 138 may perform various processing techniques on the photon signals. For example, the readout electronics unit 138 may sort the photon signals into "energy bins" based on intensity.

The embodiments described herein have been described with reference to drawings. The drawings illustrate certain details of specific embodiments that provide the systems, methods and programs described herein. However, describing the embodiments with drawings should not be construed as imposing on the disclosure any limitations that may be present in the drawings.

It should be understood that no claim element herein is to be construed under the provisions of 35 U.S.C. § 112(f), unless the element is expressly recited using the phrase "means for."

As utilized herein, terms of degree such as "approximately," "about," "substantially," and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to any precise numerical ranges provided. Accordingly, these terms should be interpreted as indicating that insubstantial or inconsequential modifications or alterations of the subject matter described and claimed are considered to be within the scope of the disclosure as recited in the appended claims.

It should be noted that terms such as "exemplary," "example," and similar terms, as used herein to describe various embodiments, are intended to indicate that such embodiments are possible examples, representations, or illustrations of possible embodiments, and such terms are not intended to connote that such embodiments are necessarily extraordinary or superlative examples.

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any element on its own or any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the drawings. It should be noted that the orientation of various elements may differ according to other exemplary embodiments, and that such variations are intended to be encompassed by the present disclosure.

As used herein, terms such as "engine" or "circuit" may include hardware and machine-readable media storing instructions thereon for configuring the hardware to execute the functions described herein. The engine or circuit may be embodied as one or more circuitry components including, but not limited to, processing circuitry, network interfaces, peripheral devices, input devices, output devices, sensors, etc. In some embodiments, the engine or circuit may take the form of one or more analog circuits, electronic circuits (e.g., integrated circuits (IC), discrete circuits, system on a chip (SOCs) circuits, etc.), telecommunication circuits, hybrid circuits, and any other type of circuit. In this regard, the engine or circuit may include any type of component for accomplishing or facilitating achievement of the operations described herein. For example, an engine or circuit as described herein may include one or more transistors, logic gates (e.g., NAND, AND, NOR, OR, XOR, NOT, XNOR, etc.), resistors, multiplexers, registers, capacitors, inductors, diodes, wiring, and so on).

An engine or circuit may be embodied as one or more processing circuits comprising one or more processors communicatively coupled to one or more memory or memory devices. In this regard, the one or more processors may execute instructions stored in the memory or may execute instructions otherwise accessible to the one or more processors. The one or more processors may be constructed in a manner sufficient to perform at least the operations described herein. In some embodiments, the one or more processors may be shared by multiple engines or circuits (e.g., engine A and engine B, or circuit A and circuit B, may comprise or otherwise share the same processor which, in some example embodiments, may execute instructions stored, or otherwise accessed, via different areas of memory).

Alternatively or additionally, the one or more processors may be structured to perform or otherwise execute certain operations independent of one or more co-processors. In other example embodiments, two or more processors may be coupled via a bus to enable independent, parallel, pipelined, or multi-threaded instruction execution. Each processor may be provided as one or more suitable processors, application specific integrated circuits (ASICs), field programmable gate arrays (FPGAs), digital signal processors (DSPs), or other suitable electronic data processing components structured to execute instructions provided by memory. The one or more processors may take the form of a single core processor, multi-core processor (e.g., a dual core processor, triple core processor, quad core processor, etc.), microprocessor, etc. In some embodiments, the one or more processors may be external to the apparatus, for example the one or more processors may be a remote processor (e.g., a cloud based processor). Alternatively or additionally, the one or more processors may be internal or local to the apparatus. In this regard, a given engine or circuit or components thereof may be disposed locally (e.g., as part of a local server, a local computing system, etc.) or remotely (e.g., as part of a remote server such as a cloud based server). To that end, engines or circuits as described herein may include components that are distributed across one or more locations.

An example system for providing the overall system or portions of the embodiments described herein might include one or more computers, including a processing unit, a system memory, and a system bus that couples various system components including the system memory to the processing unit. Each memory device may include non-transient volatile storage media, non-volatile storage media, non-transitory storage media (e.g., one or more volatile or non-volatile memories), etc. In some embodiments, the non-volatile media may take the form of ROM, flash memory (e.g., flash memory such as NAND, 3D NAND, NOR, 3D NOR, etc.), EEPROM, MRAM, magnetic storage, hard discs, optical discs, etc. In other embodiments, the volatile storage media may take the form of RAM, TRAM, ZRAM, etc. Combinations of the above are also included within the scope of machine-readable media. In this regard, machine-executable instructions comprise, for example, instructions and data which cause a general purpose computer, special purpose computer, or special purpose processing machines to perform a certain function or group of functions. Each respective memory device may be operable to maintain or otherwise store information relating to the operations performed by one or more associated circuits, including processor instructions and related data (e.g., database components, object code components, script components, etc.), in accordance with the example embodiments described herein.

Although the drawings may show and the description may describe a specific order and composition of method steps, the order of such steps may differ from what is depicted and described. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied, and the nature or number of discrete processes may be altered or varied. The order or sequence of any element or apparatus may be varied or substituted according to alternative embodiments. Accordingly, all such modifications are intended to be included within the scope of the present disclosure as defined in the appended claims. Such variation may depend, for example, on the software and hardware systems chosen and on designer choice. All such variations are within the scope of the disclosure. Likewise, software implementations of the described methods could be accomplished with standard programming techniques with rule-based logic and other logic to accomplish the various connection steps, processing steps, comparison steps, and decision steps.

The foregoing description of embodiments has been presented for purposes of illustration and description. It is not intended to be exhaustive or to limit the disclosure to the precise form disclosed, and modifications and variations are possible in light of the above teachings or may be acquired from this disclosure. The embodiments were chosen and described in order to explain the principals of the disclosure and its practical application to enable one skilled in the art to utilize the various embodiments and with various modifications as are suited to the particular use contemplated. Other substitutions, modifications, changes and omissions may be made in the design, operating conditions, and arrangement of the embodiments without departing from the scope of the present disclosure as expressed in the appended claims.

What is claimed is:

1. A computed tomography (CT) imaging system comprising:

- a detector array configured to detect X-ray projections from a source, the detector array including:
  - a semiconductor sensor array including a plurality of sensors, each sensor including:
    - a first surface of the sensor including a first dopant, wherein the first surface has a high-voltage bias and is configured to receive the X-ray projections;
    - a second surface of the sensor opposite the first surface and including a plurality of sensing regions of a second dopant, wherein the second surface has a low-voltage bias and is configured to collect a plurality of charges from the X-ray projections;
    - a substrate including a semiconductor material and the first dopant and having a resistivity of at least five kiloohm centimeters, the substrate positioned between the first surface and the second surface; and
    - a readout electronics unit positioned on the second surface and between the plurality of sensing regions, wherein a surface area of the readout electronics unit is less than one percent of a surface area of the second surface.

2. The CT imaging system of claim 1, wherein the semiconductor sensor array is an edge-illuminated semiconductor sensor array.

3. The CT imaging system of claim 1, wherein each sensing region of the plurality of sensing regions have a surface width of at least fifty micrometers and the readout electronics unit has a surface width that does not exceed ten micrometers.

4. The CT imaging system of claim 1, wherein the readout electronics unit is positioned in a readout electronics area of the second surface, and a corner from each of the plurality of sensing regions is positioned in the readout electronics area.

5. The CT imaging system of claim 4, wherein the readout electronics unit is configured to receive charges from the X-ray projections that are collected by the plurality of sensing regions in the readout electronics area.

6. The CT imaging system of claim 1, wherein a readout electronics area of the readout electronics unit is configured to prevent signal leakage into the readout electronics unit.

7. The CT imaging system of claim 1, wherein the readout electronics unit includes a depletion region, the depletion region having a width that does not exceed 0.3 micrometers.

8. The CT imaging system of claim 1, further comprising:
a first region of the readout electronics unit including the first dopant and a second region of the readout electronics unit including the second dopant, the first region and the second region configured to enable operation of one or more transistors in the readout electronics unit.

9. The CT imaging system of claim 1, wherein each sensing region of the plurality of sensing regions are configured to sense one or more photon holes from the X-ray projections, and the readout electronics unit is configured to receive a plurality of photon holes from the plurality of sensing regions.

10. The CT imaging system of claim 1, wherein the readout electronics unit is configured to at least one of amplify or process the plurality of charges received from the plurality of sensing regions.

11. A system comprising:
a semiconductor sensor array including a plurality of sensors, each sensor including:
a first surface of the sensor including a first dopant, wherein the first surface has a high-voltage bias and is configured to receive X-ray projections;
a second surface of the sensor opposite to the first surface and including a plurality of sensing regions of a second dopant, wherein the second surface has a low-voltage bias and is configured to collect a plurality of charges from the X-ray projections;
a substrate including a semiconductor material and the first dopant and having a resistivity of at least five kiloohm centimeters, the substrate positioned between the first surface and the second surface; and
a readout electronics unit positioned on the second surface and between the plurality of sensing regions, wherein a surface area of the readout electronics unit is less than one percent of a surface area of the second surface.

12. The system of claim 11, wherein the semiconductor sensor array is an edge-illuminated semiconductor sensor array.

13. The system of claim 11, wherein the readout electronics unit is positioned in a readout electronics area of the second surface, and a corner from each sensing region of the plurality of sensing regions is positioned in the readout electronics area.

14. The system of claim 11, wherein each sensing region of the plurality of sensing regions have a surface width of at least fifty micrometers and readout electronics unit has a surface width that does not exceed ten micrometers.

15. The system of claim 11, wherein a first region of the readout electronics unit includes the first dopant and a second region of the readout electronics unit includes the second dopant, the first region and the second region configured to enable operation of one or more transistors in the readout electronics unit.

16. A method for detecting X-ray projections comprising:
receiving the X-ray projections on a first surface of a semiconductor sensor;
transporting charges of the X-ray projections through a substrate, the substrate including a semiconductor material having a resistivity of at least five kiloohm centimeters;
collecting a portion of the charges, by a plurality of sensing regions on a second surface of the semiconductor sensor, the second surface being opposite the first surface; and
processing, by a readout electronics unit positioned on a region occupying less than one percent of the second surface, the portion of the charges collected by the plurality of sensing regions.

17. The method of claim 16, wherein the first surface of the semiconductor sensor has a high-voltage bias and includes a first dopant, and the second surface of the semiconductor sensor, including the plurality of sensing regions including a second dopant, has a low-voltage bias.

18. The method of claim 16, wherein the semiconductor sensor is an edge-illuminated semiconductor sensor.

19. The method of claim 16, wherein transporting the charges of the X-ray projections through the substrate includes:
generating an electric field between the first surface and the second surface; and
transferring, via the electric field, the charges from the first surface to the sensing regions through the substrate.

20. The method of claim 16, wherein processing the portion of the charges includes:
electrically isolating, by one or more regions of a first dopant or a second dopant, at least a portion of the readout electronics unit; and
amplifying, by one or more electronics within the one or more regions of the first dopant or the second dopant, the portion of charges collected by the plurality of sensing regions.

* * * * *